(12) United States Patent
Gent et al.

(10) Patent No.: US 6,852,100 B1
(45) Date of Patent: Feb. 8, 2005

(54) POUCHES FOR COLLECTING MATTER EXCRETED BY THE BODY

(75) Inventors: John A. Gent, Hampshire (GB); Graham E. Steer, London (GB)

(73) Assignee: Bristol-Myers Squibb Company, New York, NY (US)

( * ) Notice: Subject to any disclaimer, the term of this patent is extended or adjusted under 35 U.S.C. 154(b) by 0 days.

(21) Appl. No.: 09/348,954

(22) Filed: Jul. 7, 1999

(51) Int. Cl.$^7$ .................................................. A61F 5/44
(52) U.S. Cl. ..................................... 604/333; 604/337
(58) Field of Search .............................. 604/359, 360, 604/364, 367, 385.01, 385.06, 327, 332–345

(56) References Cited

U.S. PATENT DOCUMENTS

| | | | | |
|---|---|---|---|---|
| 3,856,014 A | * | 12/1974 | Yamauchi | 128/290 |
| 4,203,445 A | * | 5/1980 | Jessup et al. | 604/333 |
| 4,863,445 A | * | 9/1989 | Mayhan et al. | 604/317 |
| 5,401,264 A | * | 3/1995 | Leise, Jr. | 604/333 |
| 5,417,677 A | * | 5/1995 | Schneider et al. | 604/332 |
| 5,582,603 A | * | 12/1996 | Difilippantonio et al. | 604/380 |
| 5,643,234 A | * | 7/1997 | Lesko | 604/333 |
| 5,769,832 A | * | 6/1998 | Hasse | 604/359 |
| 5,860,959 A | * | 1/1999 | Gent | 604/332 |
| 5,868,724 A | * | 2/1999 | Dierckes, Jr. et al. | 604/368 |
| 5,885,263 A | * | 3/1999 | Gancet et al. | 604/359 |
| 5,944,704 A | * | 8/1999 | Guarracino et al. | 604/359 |
| 6,031,147 A | * | 2/2000 | Gross | 604/359 |
| 6,083,602 A | * | 7/2000 | Caldwell et al. | 428/77 |
| 6,508,794 B1 | * | 1/2003 | Palumbo et al. | 604/317 |

* cited by examiner

*Primary Examiner*—Larry I. Schwartz
*Assistant Examiner*—C. Lynne Anderson
(74) *Attorney, Agent, or Firm*—Stuart E. Krieger

(57) ABSTRACT

The present invention provides a carrier which comprises a malodour counteractant (MCA), for use in an ostomy or incontinence pouch, wherein said carrier is attached directly or indirectly to the wall of the pouch. The MCA may be in the form of a coating or a matrix on the carrier, or may be attached directly to the carrier by way of an adhesive. The invention also provides a method for use in the production of an ostomy or incontinence pouch comprising attaching directly or indirectly to plastics material forming, or for forming, a pouch wall, a carrier carrying an MCA. A preferred MCA is a hydrogen peroxide generator, for example, sodium perborate, which may be used in the above carrier, or in other delivery mechanisms.

28 Claims, 1 Drawing Sheet

POUCHES FOR COLLECTING MATTER EXCRETED BY THE BODY

FIELD OF THE INVENTION

The present invention relates to improvements relating to pouches for collecting matter excreted by the body, for example, ostomy, incontinence and/or woundcare pouches, in particular to the use of a malodour counteractant (hereinafter referred to as an MCA).

BACKGROUND TO THE INVENTION

When body effluent is collected in an ostomy pouch, unpleasant odours exist to which the human nose is highly sensitive. It is desirable (1) to avoid such malodours from escaping from the pouch while the pouch is being worn, and (2) to avoid a highly unpleasant smell emulating from the bag when it is removed for emptying, or disposal. MCAs for use in the managing of malodours released from the pouch when it is removed from the body for disposal, or in order to empty, have been known for several years.

The conventional technique of adding an MCA to an ostomy pouch is by dispersing a few drops of a fragrance, squirting a powder, or by using a capsule containing fragrance or powder. However, it is highly undesirable for the ostomate to have to physically handle chemicals of this type. Furthermore, the abovementioned techniques result, to a greater or lesser extent, in the MCA ending up in the base of the pouch, where it will tend to aggregate with minimal surface area in the form of drops or lumps of powder. For example, a capsule will fall to the base of the pouch, where it will rely on the liquid present in the body waste to release the counteractant. Eventually the capsule will release its contents at the base of the pouch, and only then will it start to counteract the malodours, working from the base upwards. This phenomenon is believed to be the cause of the performance variability commonly associated with products of this type.

An example of such a delivery technique is described in EP-A-0790047.

It would be desirable to provide an alternative system which can enable the MCAs to be placed in the pouch, for example, at the time of manufacture, and to minimise the opportunity for body waste to lie on top of the MCA.

Although the above discussion has focused on problems associated with ostomy pouches, similar problems occur with pouches for incontinence and wound care.

SUMMARY OF THE INVENTION

In one broad aspect, the invention comprises adhering a layer of MCA onto the wall of the pouch. The layer of MCA may be either directly adhered to the wall of the pouch or deposited on a carrier which is subsequently bonded onto the pouch wall.

In one embodiment, the present invention provides a carrier carrying a layer of MCA material. The carrier is attached to the wall of the pouch as it is undesirable to have anything loose within the pouch which may fall out or become mis-positioned during manufacture or transportation.

Preferably, the carrier is adhered to the wall of the pouch, such that the MCA is released from the carrier over an area close to the opening of the stoma. Thus when the body waste enters the pouch, the MCA is released from the wall of the pouch rather than the base of the pouch. Thus the position of the MCA can significantly increase the probability of affecting the malodours in the area close to the pouch opening.

It is desirable, but not essential, that the carrier be capable of absorbing excess liquid present in the effluent. Therefore, preferably the carrier possesses absorbent properties.

In all cases, the carrier may comprise any of the following;
  (a) a paper tissue (for example, a tissue containing thermoplastic fibres such as that commonly used for packaging tea in tea bags),
  (b) a plastic film (for example, polyvinyl alcohol or polyethylene);
  (c) a non-woven fabric; or
  (d) an absorbent pad.

In the instance where the carrier is an absorbent pad, this pad may, for example, be a composite comprising any of the following:
  (i) tissue paper/sodium polyacrylate, glycerol, water/tissue paper (for example, as described in GB-A-2301350);
  (ii) tissue paper/viscose and super-absorbent fibres/tissue paper,
  (iii) tissue paper/viscose and super-absorbent fibres;
  (iv) polyvinyl alcohol fibres and super-absorbent fibres.

In the above the "/" represents separate layers of the composite.

The super-absorbent fibres may be those produced under the trade name "Oasis".

Preferably, where the carrier is an absorbent pad, the MCA is adhered to the carrier in a non-continuos pattern (or grid), thus leaving clear regions to allow direct contact with the absorbent pad.

The term MCA is used broadly herein to encompass any form of malodour counteractant, and includes odour absorbers, odour maskers (e.g. fragrances), and substances which reduce the rate of bacterial growth e.g. benzyl alkonium chloride and which on release react or catalyse reactions with odorous chemicals such as oxidising agents and enzymes. The carrier might, for example, itself not contain any MCA material.

In all cases, the MCA material, components or additives may, for example, consist of one or more of the following: one or more oxidising agents or generators thereof, for example: the oxidising agent hydrogen peroxide, or a generator thereof such as sodium perborate; the oxidising agent chlorine dioxide, or a generator thereof such as sodium chlorite;

one or more iodine generators;

one or more bacterial growth inhibitors (e.g. benzyl alkonium chloride, sodium nitrite and/or sodium benzoate);

one or more enzyme systems, for example, Vegetable Protein extracts A3058 ex Carruba In a preferred embodiment of the invention, the MCA material comprises one or more hydrogen peroxide generators.

Hydrogen peroxide is an ecologically desirable pollution control agent which yields only water or oxygen on decomposition (Kirk Othmer Encyclopaedia of Chemical Technology, Vol. 13, p. 986–7 and p. 993–5). In particular, hydrogen peroxide has been used in the treatment of waste water and sewerage effluents, and to control hydrogen sulphide generated by the anaerobic reaction of raw sewerage in sewer lines or collection points, thus minimising or eliminating disagreeable odours.

Typically, the hydrogen peroxide functions as an oxidising agent, thereby resulting in the oxidation of a number of different toxic and/or noxious substances in waste water, for example hydrogen sulphide and/or other mercaptans (Joseph Salvato, Environmental Engineering and Sanitation, Wiley, p.639–40). Moreover, hydrogen peroxide is an excellent source of dissolved oxygen, and also attacks aerobic sulphide-producing organisms.

Hydrogen peroxide may also be used to remove toxic or malodorous pollutants from industrial gas streams. Many liquid phase methods have been reported for the removal of $NO_x$ gases (for example, Canadian Patent No. 960,437; U.S. Pat. No. 5,112,587; French Patent No. 2,373,327; German Patent No. 2,524,115), sulphur dioxide, reduced sulphur compounds, amines (W. H. Kibbel Jr., Ind. Water Eng. 13[4], 4, 1976; Japanese Patent 7,840,591) and phenols (Belgian Patent Nos. 863,321 and 863,322).

In one embodiment of the invention, the hydrogen peroxide generator is a metal perborate. Preferably, the perborate is sodium perborate.

Sodium perborate occurs as white crystalline granules or as a white powder. It is odourless and thus does not affect the filter system of the ostomy pouch. Although stable in cool, dry air (i.e., pouch storage conditions), sodium perborate decomposes in moist air (i.e., during wear conditions) into sodium metaborate and hydrogen peroxide, with the gradual evolution of oxygen.

The National Formulary (American Pharmaceutical Association, Washington) lists two forms of sodium perborate for use as an oxidant and as a local anti-infective agent Encyclopaedia of Industrial Chemical Analysis, Vol.7, p.379). The sodium perborate is commercially available either in the form of the tetrahydrate or the monohydrate. For example, the tetrahydrate may have the following specifications:

Formula $NaBO_3.4H_2O$,

Assay % minimum: 86.5

Available oxygen % minimum: 9.0

Heavy metals: maximum 20 ppm

The tetrahydrate has the following structure in which two peroxo groups bridge the tetrahedral boron atoms:

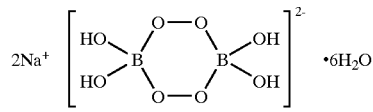

Sodium perborate is activated by temperature and moisture release. Faecal matter is at body temperature (approx. 37–38° C.) and wet, thus providing ideal conditions for sodium perborate activation. The chemical reaction is as follows:

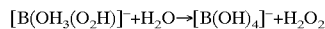

The main advantage of using sodium perborate over other hydrogen peroxide generators (such as sodium peroxide) is that it has a much greater stability and may be formulated into a wide variety of different products. Furthermore, sodium perborate is also cheap, readily available, and safe in contact with the skin.

In another embodiment of the invention, the MCA material comprises one or more chlorine dioxide generators. Preferably, the chlorine dioxide generator is sodium chlorite. This generates chlorine dioxide by virtue of the following reaction:

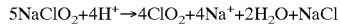

In a further embodiment, the MCA material comprises one or more iodine generators. Preferably the iodine generator is sodium iodide.

The MCA agent may be used in solid form (for example, granular or powdered form), or in a liquid form (for example, an aqueous solution of hydrogen peroxide). Solid forms (for example, on a carrier) are typically easier to handle during pouch manufacture. If a liquid form is used, then a suitable liquid-tight container, such as a rupturable capsule or pocket would then required to contain the liquid MCA until it is ready to be released by the ostomate.

In one embodiment, the MCA may comprise granules which are adhered to the carrier, for example, by adhesive. The granules might be in the form of a monolayer (in the same way as a monolayer of sand attached to a backing to form sandpaper). The monolayer of MCA granules may be applied to one side of a double sided pressure sensitive adhesive and the other side of the adhesive attached to a carrier or directly to the interior of the pouch.

The adhesive for securing the granules may, for example, be non-responsive to water, or it may be water dispersible (i.e. loses integrity in the presence of water), or more preferably water soluble, so that the adhesive dissolves almost completely. The purpose of the adhesive is to lock the granules to the carrier during the production of the pouch and subsequent storage under normal ambient conditions (e.g. in the presence of ambient water vapour and temperature), but to allow the granules to be released when contacted by liquid associated with waste body matter. To enhance bond of granules to adhesive, it may be desirable to compress granules into adhesives by use of a pressure nip.

The MCA may be applied to the carrier as a uniform film or coating. For example, techniques to produce the coating may include hot melt coating; powder coating followed by compression; powder coating on to a pressure sensitive adhesive; solvent coating; and printing.

The carrier may, if desired, be encased by a liquid permeable cover, thereby preventing any irritation which may result from direct contact between the MCA and the stoma.

In another embodiment, the present invention provides a carrier which comprises a hygroscopic matrix and one or more MCA additives. Typically, the carrier is a solid strip coated with a matrix into which one or more MCA additives are blended. The hygroscopic matrix is solid at ambient temperature and humidity, but delivers the MCA into the pouch when subjected to body temperature and high humidity, by absorbing water to form an aqueous solution or dispersion of MCA which may then interact with body waste to reduce the level of malodours evolved.

The carrier is preferably attached to a wall of the pouch.

Preferred hygroscopic matrices are illustrated by glycerol and polyethylene glycol, which may be utilised with one or more surfactants (e.g. sodium lauryl sulphate) and/or one or more soaps (e.g. sodium stearate or potassium laurate). Within an ostomy pouch, when it is being worn in use, there is a temperature of about 37° C. and a high humidity. This high humidity arises from both the stoma itself and the presence of any body waste in the bag. When subjected to high humidity and a temperature of about 37° C., the hygroscopic matrix absorbs water from the atmosphere in the bag or from direct contact with the body waste and forms a cream or paste. As water is progressively absorbed, the hygroscopic matrix physically changes, progressing from a solid through a viscous paste to a water-like consistency, thereby releasing the active MCA ingredients into the pouch in a controlled manner.

In a further aspect, the invention provides a pouch for collecting matter excreted from the body (for example, an ostomy, incontinence or wound care pouch), the pouch containing or comprising an oxidising agent generator. Prefereably, the generator is a hydrogen peroxide generator, preferably, the hydrogen peroxide generator is a metal perborate, for example, sodium perborate.

In a further aspect, the invention provides a pouch for collecting matter excreted from the body, the pouch containing or comprising a metal perborate (for example, sodium perborate).

Broadly speaking, a further aspect of the invention provides a method for use in pouch production, the method comprising attaching directly or indirectly to plastics material forming, or for forming, a pouch wall, a carrier carrying an MCA. For example, the carrier may be attached using an opposite surface to that carrying the MCA.

In another aspect, the invention provides a method of manufacturing an ostomy or incontinence pouch, the method comprising the above method steps.

In a further aspect, the invention provides an ostomy or incontinence pouch including a carrier as defined above (and carrying MCA material). Preferably the carrier is attached directly or indirectly to the interior of the pouch.

DESCRIPTION OF THE DRAWINGS

Embodiments of the invention are now described by way of example only, with reference to the accompanying drawings, in which.

DESCRIPTION OF PREFERRED EMBODIMENTS

Figure 1:
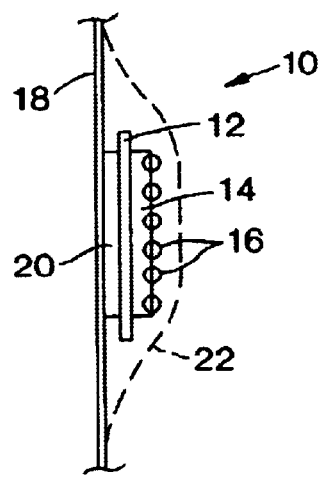
FIG. 1 is a schematic section through a first MCA and carrier.

Referring to FIG. 1, a first article 10 consists of a carrier 12 having on a first face a layer of adhesive 14 and a monolayer of particles of powdered MCA 16 (for example, sodium perborate granules, or sodium chlorite granules). The other face of the carrier is attached to the interior face of a plastics wall 18 of an ostomy pouch, either by welding the pouch directly to the carrier, or by means of a second layer of adhesive 20. In order to prevent direct contact between the MCA powder, and a patient's stoma, a liquid permeable cover is secured over the article 10. The cover can be secured to the plastics wall 18 by welding, or by adhesive.

The layers 14 and 20 may be of the same adhesive, or they may be of different adhesives. The adhesives may be pressure sensitive. Preferably, at least the layer 14 is water dispersible, or water soluble.

The film 12 and the adhesive layers 14 and 20 may be formed as a double-sided adhesive tape.

Figure 2:
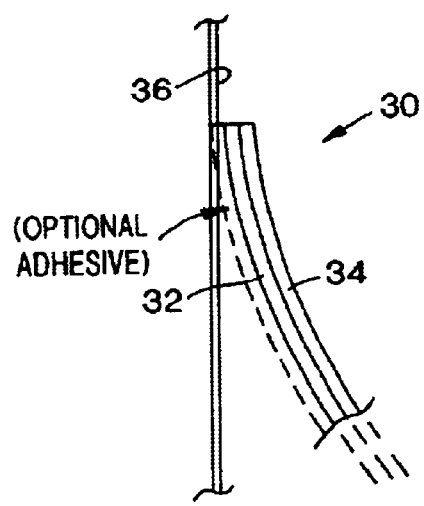
FIG. 2 is a schematic section illustrating a second MCA and carrier.

Referring to FIG. 2, a second article 30 consists of a carrier 32 to which is applied a coating 34 consisting of a matrix and one or more MCA additives. The carrier 32 is secured at one end to the interior face of a plastics pouch wall 36, for example, by adhesive or by welding.

Figure 3:
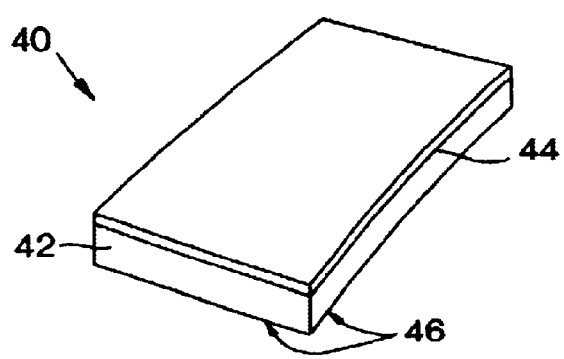
FIG. 3 is a schematic view illustrating a third MCA and carrier.

In the above examples, the carrier is passive (in other words, it has no purpose except to carry the MCA). Referring to FIG. 3, in other embodiments, the carrier may consist of a pad, for example, an absorbent pad. Alternatively, the carrier may be passive, but may be secured to another article, for example, an absorbent pad, which is itself attached to the interior face of the pouch wall.

In FIG. 3, the pad 40 consists of a pad containing super-absorbent material 42, and a surface layer of MCA 44 (either carrier directly on the pad, or on a carrier bonded to the pad). In one form, the MCA layer may be apertured to allow moisture direct access to the super-absorbent containing pad. The pad 40 would be adhered to the wall of a plastics pouch by its undersurface 46 as seen in FIG. 3. The pad 40 could be bonded to the wall along the pad length, or at one or more discrete positions, for example, at one or both ends of the pad.

If the pad is attached to wall at only one end (in the same way as illustrated in FIG. 2), then the pad may be able to float relative to the wall, thus allowing liquid to be absorbed through the undersurface 46 of the pad (as seen in FIG. 3). This may, in some cases, avoid the need to have to aperture the MCA 44 on the front surface.

The present invention is further illustrated by way of the following non-limiting example.

EXAMPLE

A sheet of paper with a heat-sealable surface such as that used in the manufacture of Tea Bags (supplied by J R Crompton Ltd Co., PV314) was placed with the non heat sealable surface uppermost. To this surface was adhered a double sided pressure sensitive adhesive which did not interact with the perborate, such as that supplied by R G. H. Rubber and Plastics Ltd under code Mactac B1148.

On to the resultant exposed pressure sensitive adhesive surface was sprinkled an excess of particles of sodium perborate which were spread across the adhesive surface, such that the adhesive was covered. The resultant coated composite was then squeezed in a nip, and excess sodium perborate particles removed. The coating weight of sodium perborate was 252 gsm (grams per square meter).

The sheet was cut into 100 mm×50 mm pads such that each pad had approximately 1.26 grams of sodium perborate.

A coated strip was then thermally welded through the heat sealable surface of the paper layer to a coextruded film comprising two ethylene vinyl acetate outer layers and a polyvinylidene chloride copolymer core. The resultant film with coated strip was converted into a colostomy pouch. The resultant pouch, designated Pouch A was then used to contain fresh faecal matter. The pouch was then effectively closed and maintained at body temperature for a period of 30 minutes.

For comparative purposes an uncoated strip of Crompton PV 314 was thermally welded through the heat sealable layer to a coextruded film comprising two ethylene vinyl acetate outer layers and a polvinylidene chloride copolymer core. The resultant film with uncoated strip was converted into a colostomy pouch. The resultant pouch designated Pouch B was then used to contain fresh faecal matter, and subjected to the same conditions as pouch A.

After a period of 30 minutes, the pouches were opened, and it was noted that there was considerably less malodour emanating from Pouch A as compared with Pouch B. This exercise was repeated on a further four comparisons, using the same odour testing panel, and the same findings were observed.

With the designs described hereinbefore, the MCA can remain stable, with very little or no deterioration occurring before the pouch is used. The MCA components are only released into the pouch when the pouch is worn and contacted by body effluent. The MCA can be released at a desired position in the pouch interior, for example, close to the entrance aperture. The above techniques also enable the article to be secured within a pouch during manufacture of the pouch, to prevent the MCA from moving around undesirably during pouch manufacture. Furthermore, there is also very little (if any) hazard to manufacturing staff who have to handle the product and the pouches during manufacture.

It will be appreciated that the foregoing description is merely illustrative of preferred forms of the invention, and that many modifications may be made within the principles of the invention. The applicant claims protection for any novel feature described herein and/or illustrated in the drawings, whether or not emphasis has been placed thereon.

What is claimed is:

1. An ostomy pouch for collecting waste excreted from a human body through a stoma, the pouch including an envelope formed of a plastic material defining a waste collection chamber, said envelope having an interior surface portion, the envelope having an opening for encircling a stoma, the envelope fitting to the human body around the stoma, the envelope having a carrier including an absorbent pad that carries and releases at least one malodour counteractant, said carrier being fixedly attached directly or indirectly to the interior surface portion of the envelope near the stomal opening, said carrier being encased against said interior surface portion by a liquid permeable cover, said carrier being unvented directly to the exterior of the pouch, said cover preventing direct contact of said malodour conteractant by a stoma while permitting the body waste to contact the absorbent pad, said absorbent pad being a composite of one or more of the following:
   (i) separate layers of; (1) tissue paper, (2) sodium polyacrylate, glycerol, water, and (3) tissue paper;
   (ii) separate layers of; (1) tissue paper, (2) viscose and super-absorbent fibres, and (3) tissue paper;
   (iii) separate layers of; (1) tissue paper, (2) viscose and super-absorbent fibres; and
   (iv) polyvinyl alcohol fibres and super-absorbent fibres.

2. The ostomy pouch according to claim 1, wherein the malodour counteractant is a coating on part, or all, of a surface of the carrier.

3. The ostomy pouch according to claim 1, wherein the malodour counteractant is adhered to the carrier by means of an adhesive.

4. The ostomy pouch according to claim 1, wherein said carrier carries a matrix and at least one malodour counteractant.

5. The ostomy pouch according to claim 4, wherein the matrix is a hygroscopic matrix.

6. The ostomy pouch according to claim 4, wherein the matrix comprises glycerol and polyethylene glycol.

7. The ostomy pouch according to claim 4, wherein the matrix comprises one or more surfactants.

8. The ostomy pouch according to claim 4, wherein the matrix comprises one or more soaps.

9. The ostomy pouch according to claim 1, wherein the malodour counteractant is an oxidising agent generator.

10. The ostomy pouch according to claim 1, wherein the malodour counteractant comprises a hydrogen peroxide generator.

11. The ostomy pouch according to claim 1, wherein the malodour counteractant comprises a chlorine dioxide generator.

12. The ostomy pouch according to claim 10, wherein the hydrogen peroxide generator is a metal perborate.

13. The ostomy pouch according to claim 12, wherein the metal perborate is sodium perborate.

14. The ostomy pouch according to claim 1, wherein the malodour counteractant comprises one or more antibacterial agents and/or one or more fragrance additives.

15. The ostomy pouch according to claim 1, wherein the carrier is heat sealed, or welded to the interior surface portion of the envelope.

16. The ostomy pouch according to claim 1, wherein the malodour counteractant is effective in reducing the odor of excreted bodily fluid as smelled by a user of the pouch.

17. An ostomy pouch for collecting waste excreted from a human body through a stoma, the pouch including an envelope formed of a plastic material defining a waste collection chamber, said envelope having an interior surface portion, the envelope having an opening for encircling a stoma, the envelope fitting to the human body around the stoma, the envelope having a carrier including an absorbent pad that carries and releases at least one malodour counteractant, said malodour counteractant including a chlorine dioxide generator, said carrier being fixedly attached directly or indirectly to the interior surface portion of the envelope near the stomal opening, said carrier being encased against said interior surface portion by a liquid permeable cover, said carrier being unvented directly to the exterior of the pouch, said cover preventing direct contact of said malodour conteractant by a stoma while permitting the body waste to contact the absorbent pad.

18. The ostomy pouch according to claim 17, wherein the malodour counteractant is a coating on part, or all, of a surface of the carrier.

19. The ostomy pouch according to claim 17, wherein the malodour counteractant is adhered to the carrier by means of an adhesive.

20. The ostomy pouch according to claim 17, wherein said carrier carries a matrix and at least one malodour counteractant.

21. The ostomy pouch according to claim 20, wherein the matrix is a hygroscopic matrix.

22. The ostomy pouch according to claim 20, wherein the matrix comprises glycerol and polyethylene glycol.

23. The ostomy pouch according to claim 20, wherein the matrix comprises one or more surfactants.

24. The ostomy pouch according to claim 20, wherein the matrix comprises one or more soaps.

25. The ostomy pouch according to claim 17, wherein the absorbent pad is a composite comprising one or more of the following:
   (i) separate layers of; (1) tissue paper, (2) sodium polyacrylate, glycerol, water, and (3) tissue paper;
   (ii) separate layers of; (1) tissue paper, (2) viscose and super-absorbent fibres, and (3) tissue paper,
   (iii) separate layers of; (1) tissue paper, (2) viscose and super-absorbent fibres; and
   (iv) polyvinyl alcohol fibres and super-absorbent fibres.

26. The ostomy pouch according to claim 17, wherein the malodour counteractant includes one or more antibacterial agents and/or one or more fragrance additives.

27. The ostomy pouch according to claim 17, wherein the carrier is heat sealed, or welded to the interior surface portion of the envelope.

28. The ostomy pouch according to claim 17, wherein the malodour counteractant is effective in reducing the odor of excreted bodily fluid as smelled by a user of the pouch.

* * * * *